US007834235B2

(12) United States Patent
Long et al.

(10) Patent No.: US 7,834,235 B2
(45) Date of Patent: *Nov. 16, 2010

(54) SYSTEM FOR INTERACTIVELY TRAINING A CHILD AND A CAREGIVER TO ASSIST THE CHILD TO OVERCOME BEDWETTING

(75) Inventors: Andrew M. Long, Appleton, WI (US); Thomas M. Ales, III, Neenah, WI (US); Meghan E. Collins, Lakemoor, IL (US)

(73) Assignee: Kimberly-Clark Worldwide, Inc.

( * ) Notice: Subject to any disclaimer, the term of this patent is extended or adjusted under 35 U.S.C. 154(b) by 1073 days.

This patent is subject to a terminal disclaimer.

(21) Appl. No.: 11/514,507

(22) Filed: Aug. 31, 2006

(65) Prior Publication Data

US 2008/0058745 A1 Mar. 6, 2008

(51) Int. Cl.
*A61F 13/20* (2006.01)
*G08B 13/14* (2006.01)
*G08B 21/00* (2006.01)

(52) U.S. Cl. .................. 604/361; 340/573.5; 340/573.6; 340/604

(58) Field of Classification Search ................. 604/361, 604/362, 367, 364, 380; 340/572.5, 604, 340/572.4, 573.6, 596, 573.5; 607/96, 108, 607/114
See application file for complete search history.

(56) References Cited

U.S. PATENT DOCUMENTS

| 3,460,123 | A | 8/1969  | Bass             |
| 3,592,195 | A | 7/1971  | Van Wagenen et al. |
| 3,810,140 | A | 5/1974  | Finley           |
| 4,191,950 | A | 3/1980  | Levin et al.     |
| 4,271,406 | A | 6/1981  | Wilson           |
| 4,356,479 | A | 10/1982 | Wilson           |
| 4,356,818 | A | 11/1982 | Macias et al.    |
| 4,507,121 | A | 3/1985  | Leung            |
| 4,539,559 | A | 9/1985  | Kelly et al.     |
| 4,704,108 | A | 11/1987 | Okada et al.     |
| 4,704,116 | A | 11/1987 | Enloe            |
| 4,738,260 | A | 4/1988  | Brown            |
| 4,800,370 | A | 1/1989  | Vetecnik         |

(Continued)

FOREIGN PATENT DOCUMENTS

EP 0 911 000 A1 4/1999

(Continued)

*Primary Examiner*—Jacqueline Stephens
(74) *Attorney, Agent, or Firm*—Randall W. Fieldhack; Michael J. Bendel (57) ABSTRACT

A system for interactively training a child and a caregiver to assist the child to overcome bedwetting. The system includes an absorbent article, a urine insult detector, a urine insult event communicator and a urine insult event alarm. The urine insult event alarm includes a local alarm proximate the child and a remote alarm proximate the caregiver. The urine insult event alarm can inform both the child and the caregiver upon occurrence of a urine insult event and thereby provide a first interactive training opportunity to assist the child to overcome bedwetting. The local alarm includes a sensor which senses a condition of the child's environment in conjunction with the occurrence of the urine insult event and wherein the remote alarm can be selectively deactivated based on the condition and thereby provide a second interactive training opportunity to assist the child to overcome bedwetting.

18 Claims, 6 Drawing Sheets

U.S. PATENT DOCUMENTS

| | | | |
|---|---|---|---|
| 4,940,464 A | 7/1990 | Van Gompel et al. |
| 4,977,906 A | 12/1990 | Di Scipio |
| 5,036,859 A | 8/1991 | Brown |
| 5,043,704 A | 8/1991 | Blakeney |
| 5,046,272 A | 9/1991 | Vogt et al. |
| 5,074,317 A | 12/1991 | Bondell et al. |
| 5,104,116 A | 4/1992 | Pohjola |
| 5,114,781 A | 5/1992 | Morman |
| 5,116,662 A | 5/1992 | Morman |
| 5,137,033 A | 8/1992 | Norton |
| 5,224,405 A | 7/1993 | Pohjola |
| 5,291,181 A | 3/1994 | DePonte |
| 5,341,127 A | 8/1994 | Smith |
| 5,392,032 A | 2/1995 | Kline et al. |
| 5,459,452 A | 10/1995 | DePonte |
| 5,469,146 A | 11/1995 | Gurler |
| 5,486,166 A | 1/1996 | Bishop et al. |
| 5,490,846 A | 2/1996 | Ellis et al. |
| 5,537,095 A | 7/1996 | Dick et al. |
| 5,557,236 A | 9/1996 | Monti |
| 5,557,263 A | 9/1996 | Fisher et al. |
| 5,645,542 A | 7/1997 | Anjur et al. |
| 5,766,389 A | 6/1998 | Brandon et al. |
| 5,790,036 A | 8/1998 | Fisher et al. |
| 5,820,973 A | 10/1998 | Dodge, II et al. |
| 5,845,644 A | 12/1998 | Hughes et al. |
| 5,883,028 A | 3/1999 | Morman et al. |
| 5,964,743 A | 10/1999 | Abuto et al. |
| 6,072,384 A | 6/2000 | Baker |
| 6,101,366 A | 8/2000 | Castillo |
| 6,231,557 B1 | 5/2001 | Krautkramer et al. |
| 6,319,208 B1 | 11/2001 | Abita et al. |
| 6,362,389 B1 | 3/2002 | McDowall et al. |
| 6,552,245 B1 | 4/2003 | Roessler et al. |
| 6,559,772 B2 | 5/2003 | Zand et al. |
| 6,580,013 B1 | 6/2003 | Belloso |
| 6,583,722 B2 | 6/2003 | Jeutter et al. |
| 6,603,403 B2 | 8/2003 | Jeutter et al. |
| 6,641,134 B1 | 11/2003 | Dobbertin et al. |
| 6,645,190 B1 | 11/2003 | Olson et al. |
| 2002/0145525 A1 | 10/2002 | Friedman et al. |
| 2005/0285941 A1 | 12/2005 | Haigh et al. |

FOREIGN PATENT DOCUMENTS

| | | |
|---|---|---|
| EP | 0 997 125 A1 | 5/2000 |
| GB | 2 272 093 A | 5/1994 |
| JP | 08-024292 A | 1/1996 |
| WO | WO 00/37009 A2 | 6/2000 |
| WO | WO 02/15141 A1 | 2/2002 |
| WO | WO 03/051254 A2 | 6/2003 |

SYSTEM FOR INTERACTIVELY TRAINING A CHILD AND A CAREGIVER TO ASSIST THE CHILD TO OVERCOME BEDWETTING

BACKGROUND OF THE INVENTION

The present invention relates generally to absorbent articles intended for personal wear, and more particularly to such an absorbent article as part of a system to interactively train a child and assist his/her caregiver trying to overcome enuresis or bedwetting.

Disposable absorbent articles find widespread use as personal care products such as diapers, children's toilet training pants and other infant and child care products, adult incontinence garments and other adult care products. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

Disposable absorbent training pants, in particular, are useful in toilet training children. Typically, these disposable undergarments are similar to washable, cloth underwear in the manner in which they are put on and worn, yet provide an absorbent function similar to diapers to help maintain skin health. Training pants provide a child undergoing toilet training with an undergarment that eases the transition from diapers to washable, cloth underwear as they become more confident in their ability to use the toilet independently.

In order to learn to use the toilet independently, a child must first learn to recognize when urination is occurring. Because urination may often occur during an activity that distracts the child to the extent that the child does not notice urination, e.g., during sleep such as when in a bed, this recognition can represent a substantial hurdle in the training process. Also, a child's ability to recognize when urination occurs may be hampered by the improved performance of disposable absorbent undergarments which quickly draw and retain urine away from the wearer's skin after an insult occurs.

One study indicates that roughly 5%, or 3.2 million, of the estimated 61.3 million (based on the U.S. Census Bureau Profile of General Demographic Characteristics for 2000, where the number of individuals 5-19 years of age is cited as 61,297,467, and thus it is assumed that there as many individuals 4-18 years of age (also a 15-year age range)) United States children 4-18 years of age (inclusive) are enuretic. In this study the definition of enuretic is at least 1 overnight wetting accident in a 2-week period while sleeping and "frequently enuretic" is defined as experiencing at least 2 overnight wetting accidents in a 1-week period while sleeping. This study found that that 2.6%, or 1.6 MM, of the children 4-18 years of age (inclusive) are frequent enuretics.

Close monitoring of a toilet-training child by a caregiver can be helpful in that when urination occurs it can be addressed by the child and caregiver to enhance and improve the learning experience, particularly when a child is learning to wake up from sleeping to go to the bathroom. Therefore, it is beneficial to provide the caregiver with immediate notification and/or verification that urination has occurred so that it may be addressed with the child very soon after the event has occurred.

However, as a child starts to learn to wake up on their own, then less involvement by the caregiver is desirable. This can have the dual benefit of helping the child feel more confident in his/her ability to toilet train on their own, even at night, and also not disturbing the caregiver unnecessarily when the child has made significant progress toward waking him/her self.

Several attempts have been made at improving toilet training aids for toilet training pants. For example, training pants that include a temperature change member and/or a dimensional change member which provide a temperature or pressure change sensation to alert the child wearing the pants that urination has occurred have been disclosed. Additional training aids have been used to alert the caregiver and/or child that urination has occurred. Such training aids include audible alarms, vibration sensors, and light indicators that may provide visual or other sensory indication of urination.

Existing training pants having one or more training aids that alert only the wearer, or only the caregiver, to an insult of the pants do not as readily enable positive interactive training opportunities and miss helping the child in the overnight training process when caregiver involvement is most needed. One of the first obstacles to successful toilet training is helping the child become conscious of the impending occurrence of a urine insult by the child, and this is hard to accomplish if the child is completely unconscious in a deep sleep. There is a need, therefore, to provide a suitable system for interactively training a child and enabling the caregiver to assist to enhance the toilet training experience for both the child and the caregiver and help the child to better and/or more quickly overcome enuresis or bedwetting.

SUMMARY OF THE INVENTION

In one aspect of the present invention, there is provided a system for interactively training a child and a caregiver to assist the child to overcome bedwetting. The system includes an absorbent article proximate the child, with the absorbent article including a urine insult detector which detects a urine insult event. The urine insult detector is operatively coupled with a urine insult event communicator which communicates an occurrence of the urine insult event to a urine insult event alarm. The urine insult event alarm includes a local alarm proximate the child and a remote alarm proximate the caregiver where the urine insult event alarm can inform both the child and the caregiver upon occurrence of the urine insult event and thereby provide a first interactive training opportunity to assist the child to overcome bedwetting. The local alarm includes a sensor which senses a condition of the child's environment in conjunction with the occurrence of the urine insult event and where the remote alarm can be selectively activated and deactivated based on the condition and thereby provide a second interactive training opportunity to assist the child to overcome bedwetting.

In another aspect of the present invention, there is provided a system for interactively training a child and a caregiver to assist the child to overcome bedwetting. The system includes an absorbent article proximate the child, with the absorbent article including a urine insult detector which detects a urine insult event. The urine insult detector is operatively coupled with a urine insult event communicator which communicates an occurrence of the urine insult event to a urine insult event alarm. The urine insult event alarm includes a local alarm proximate the child and a remote alarm proximate the caregiver where the local alarm informs the child first to the occurrence of the urine insult event and the remote alarm is delayed in informing the caregiver to the occurrence of the urine insult event and thereby provides a first interactive training opportunity to assist the child to overcome bedwetting. The local alarm includes a sensor which senses a condition of the child's environment in conjunction with the occurrence of the urine insult event and where the remote alarm is not activated based on the condition and thereby provides a second interactive training opportunity to assist the child to overcome bedwetting.

In still another aspect of the present invention, there is provided a system for interactively training a child and a caregiver to assist the child to overcome bedwetting. The system includes an absorbent article proximate the child, with the absorbent article including a urine insult detector which detects a urine insult event. The urine insult detector is operatively coupled with a urine insult event communicator which communicates an occurrence of the urine insult event to a urine insult event alarm. The urine insult event alarm includes a local alarm proximate the child and a remote alarm proximate the caregiver where (i) in a first mode the urine insult event alarm informs the child and the caregiver simultaneously of the occurrence of the urine insult event and thereby provides a first interactive training opportunity to assist the child to overcome bedwetting and (ii) in a second mode the local alarm informs the child first to the occurrence of the urine insult event and the remote alarm is delayed in informing the caregiver to the occurrence of the urine insult event and thereby provides a second interactive training opportunity to assist the child to overcome bedwetting. The local alarm includes a sensor which senses a condition of the child's environment in conjunction with the occurrence of the urine insult event and where the remote alarm is (i) in the first mode deactivated based on the condition and thereby provides a third interactive training opportunity to assist the child to overcome bedwetting and (ii) in the second mode is not activated based on the condition and thereby provides a fourth interactive training opportunity to assist the child to overcome bedwetting.

Other features of the invention relate to the type of absorbent article, configuration of the system and its components, and a condition of the child's environment.

Still other features of the invention will be in part apparent and in part pointed out hereinafter as well as better understood by practice of the invention.

BRIEF DESCRIPTION OF THE DRAWINGS

Corresponding reference characters indictate corresponding parts throughout the drawings.

DETAILED DESCRIPTION

Figure 2:
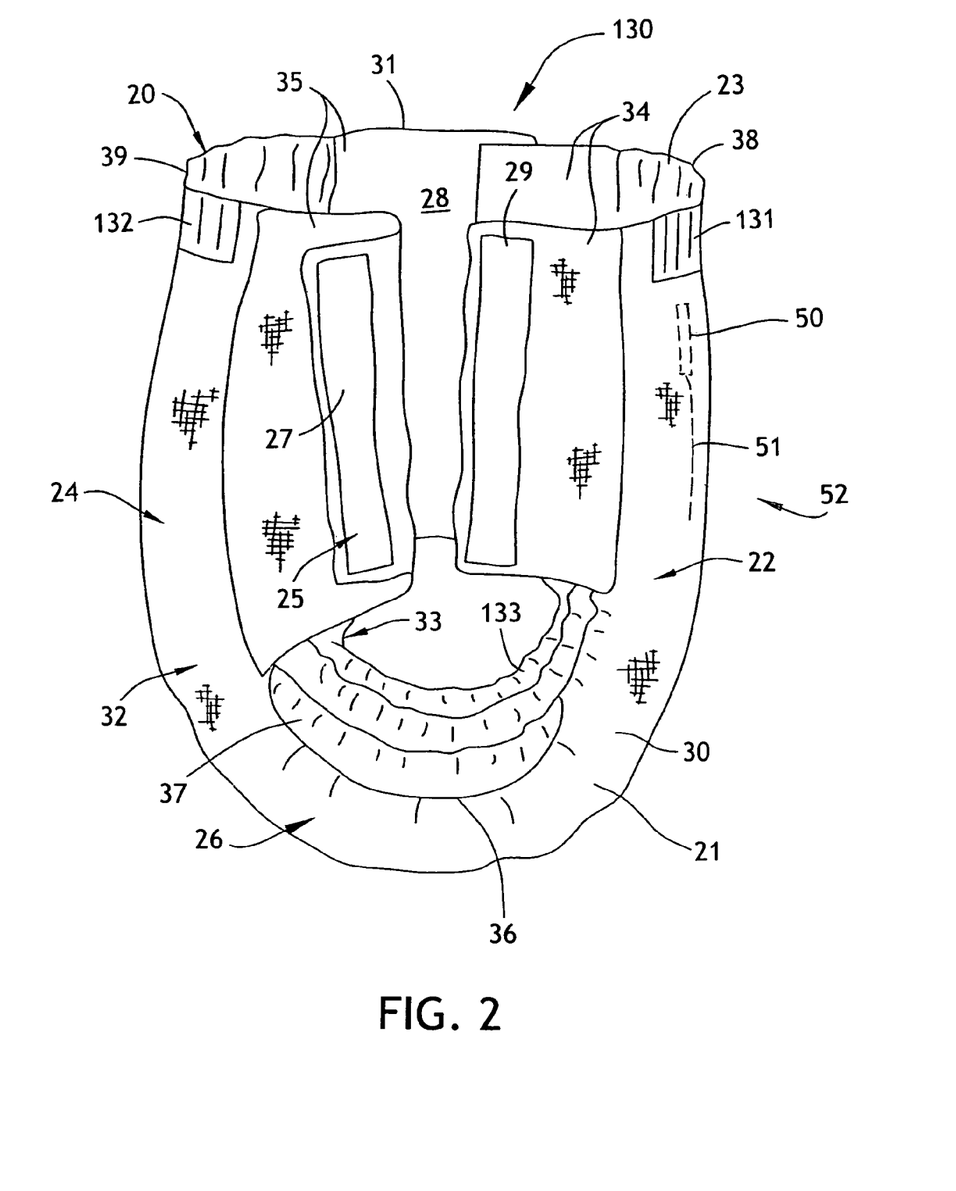
FIG. 2 representatively shows a side perspective view of an absorbent article of the present invention shown in the form of a pair of training pants having a mechanical fastening system fastened on one side of the training pants and unfastened on the opposite side thereof.
Figure 3:
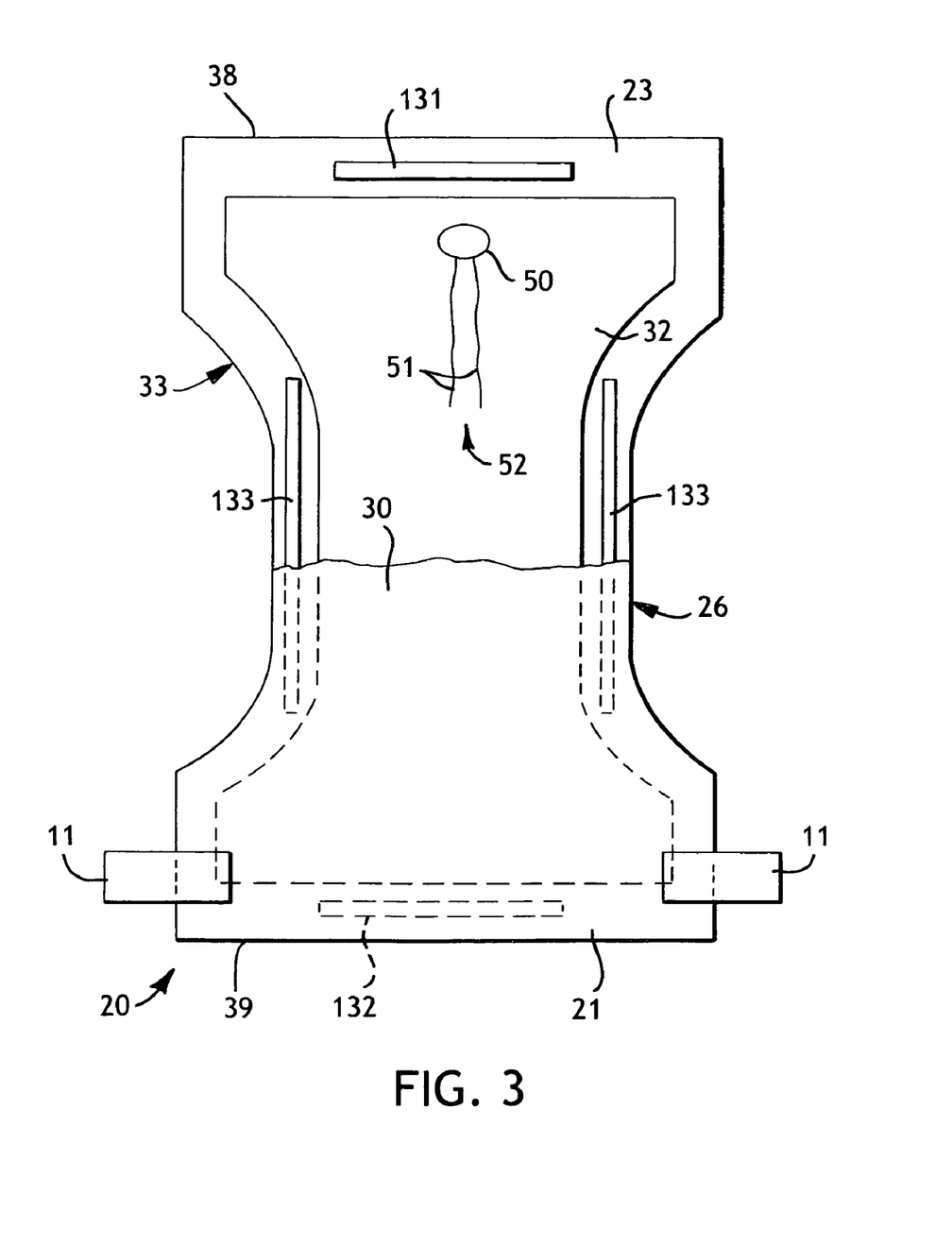
FIG. 3 representatively shows a partially cut-away, top plan view of an outward side of an absorbent article of the present invention shown in the form of a diaper.
Figure 4:
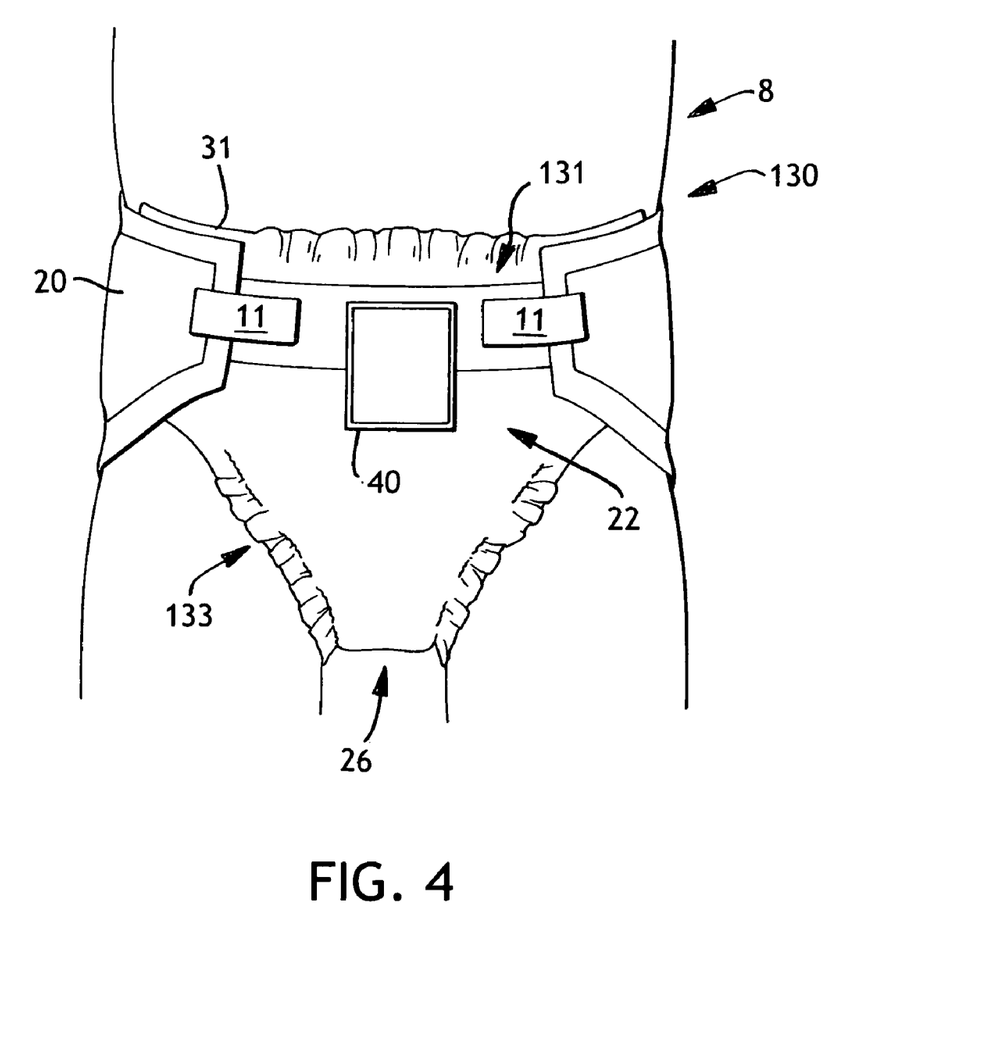
FIG. 4 representatively shows a front view of an outward side of an absorbent article of the present invention shown in the form of a diaper and which has been placed on a child; and, FIG. 5A and 5B representatively shows a flow chart of alternative configurations of the present invention.

Referring now to the drawings and in particular to FIGS. 2-4, an absorbent article of the present invention is representatively illustrated therein in the form of a child's toilet training pant and diaper and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, diaper pants, and other personal care or health care garments, and the like without departing from the scope of the present invention.

Without being limited to a theory of understanding, it is believed that children need to become acclimated to wake to the informing of an alarm (e.g., by sound or other sensory perceptible action), because children are deep sleepers (and, bedwetters even more so than non-bedwetting children). After a caregiver rouses the child for a few days to as much as a few weeks during the enuresis event, children better and/or more easily learn to wake on their own to the informing by a local alarm, e.g., sound. In this way, the child can better wake right as the insult starts, allowing him/her to finish urinating at the toilet. Further, conventionally available research indicates that up to 70% of children can be "cured" of enuresis/bedwetting by consistently using an alarm near the child. However, existing enuresis training devices have a high drop-out rate after initial usage, which is due, at least in part, to an alarm that uses very high sound volumes in the child's room because such is required to wake a deeply sleeping child and rouse a caregiver from a remote location, e.g., down the hall. The result is the overwhelming disruption wakes the caregiver and others in the whole house, and often not the enuretic child who is sleeping deeply and not yet conditioned to be awakened by the alarm, and so the alarm is not used much after initial use, and yet before the child can be effectively conditioned to awaken before enuresis. Accordingly, among other aspects, the two part alarm of the present invention enables the informing action (e.g., by sound volume or other ways) to be reduced and targeted to where it is needed (i.e., the child and the caregiver, or the child alone) and be more effective for conditioning the child. This can have the added benefit, as desired, to reduce disruption to the remainder of the household and/or help decrease the drop out rate for use of the local alarm.

As used throughout the specification and claims, the word "child" is not limited to a particular age of a person, but rather is used to refer to the inability of the person to make it through a sleeping period (e.g., of a few hours to several hours such as overnight) without having a urine insult event (e.g., enuresis). In children, enuresis is normal and as the child matures he/she trains his/her body to become more able to control urine discharge, during both waking and sleeping hours. After a certain age/maturity, if a person has enuresis such is often referred to as a medical condition. The present invention includes both situations, as well as other similar ones, and the reference to "child" means only that the condition of enuresis is being addressed, and particularly in conjunction with the activity of sleeping such as in a bed.

By way of illustration only, various materials and methods for constructing training pants (FIG. 2) such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

The pair of training pants 20 is illustrated in FIG. 2 in a partially fastened condition. The pants 20 define a longitudinal direction and a lateral direction perpendicular to the longitudinal direction. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 include those portions of the pants 20, which when worn, wholly or partially cover or encircle the waist 130 or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use (e.g., positioned relative to the other components of the pants 20) to be disposed toward the wearer, and an outer surface 30 opposite the inner surface. The pair of training pants 20 has a pair of laterally opposite side edges and a pair of longitudinally opposite waist edges (broadly, longitudinal ends), respectively designated front waist edge 38 and back waist edge 39.

The illustrated pants 20 include an absorbent assembly, generally indicated at 32, and a fastening system for securing the pants in a three-dimensional pants configuration. In the aspect of FIG. 2, the training pants 20 include a generally rectangular central absorbent assembly 32 and side panels 34, 35 formed separately from and secured to the central absorbent assembly. The side panels 34, 35 are permanently bonded along seams to the central absorbent assembly 32 in the respective front and back waist regions 22 and 24 of the pants 20. More particularly, the front side panels 34 can be permanently bonded to and extend transversely outward beyond side margins of the absorbent assembly 32 at the front waist region 22, and the back side panels 35 can be permanently bonded to and extend transversely outward beyond the side margins of the absorbent assembly at the back waist region 24. The side panels 34 and 35 may be bonded to the absorbent assembly 32 using attachment means known to those skilled in the art such as adhesive, thermal or ultrasonic bonding.

The front and back side panels 34 and 35, upon wearing of the pants 20, thus include the portions of the training pants 20 which are positioned on the hips of the wearer. The front and back side panels 34 and 35 can be permanently bonded together to form the three-dimensional configuration of the pants 20, or be releasably connected with one another such as by the fastening system 80 of the illustrated aspects. Suitable elastic materials, as well as one process of incorporating elastic side panels into training pants, are described in the following U.S. Patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference in their entirety to the extent they are consistent (i.e., not in conflict) herewith. In particular aspects, the elastic material may include a stretch-thermal laminate (STL), a neck-bonded laminate (NBL), a reversibly necked laminate, or a stretch-bonded laminate (SBL) material. As is known in the art, the side panels 34, 35 may include elastic material or stretchable but inelastic materials.

The absorbent assembly 32 is illustrated as having a rectangular shape. However, it is contemplated that the absorbent assembly 32 may have other shapes (e.g., hourglass, T-shaped, I-shaped, and the like) without departing from the scope of this invention. It is also understood that the side panels 34, 35 may instead be formed integrally with the absorbent assembly 32 without departing from the scope of this invention. In such a configuration, the side panels 34 and 35 and the absorbent assembly would include at least some common materials, such as the bodyside liner 23, outercover 21, other materials and/or combinations thereof.

The absorbent assembly 32 includes an outer cover 21 and a bodyside liner 23 in a superposed (opposed) relation therewith. The liner 23 can be suitably joined to the outer cover 21 along at least a portion of the longitudinal ends of the pants 20. The liner 23 can be suitably adapted, i.e., positioned relative to the other components of the pants 20, for contiguous relationship with the wearer's skin during wear of the pants. The absorbent assembly 32 also includes an absorbent structure disposed between the outer cover 21 and the bodyside liner 23 for absorbing liquid body exudates exuded by the wearer.

With the training pants 20 in the partially fastened position as illustrated in FIG. 2, the front and back waist regions are connected together by the fastening system 25 to define the three-dimensional pants configuration having a waist opening 31 and a pair of leg openings 33. The front and back waist edges 38 and 39 (e.g., longitudinal ends) of the training pants 20 are configured to encircle the waist of the wearer to define the waist opening 31 (FIG. 1) of the pants.

The illustrated fastening system 25 includes laterally opposite first fastening components 27 adapted for refastenable engagement to corresponding laterally opposite second fastening components 29. In one aspect, a front or outer surface of each of the fastening components 27, 29 includes a plurality of engaging elements. The engaging elements of the first fastening components 27 are adapted to repeatedly engage and disengage corresponding engaging elements of the second fastening components 29 to releasably secure the pants 20 in its three-dimensional configuration. The fastening components 27, 29 can include any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The pants 20 may further include a pair of containment flaps 37 for inhibiting the lateral flow of body exudates. As illustrated in FIG. 2, the containment flaps 37 can be operatively attached to the pants 20 in any suitable manner as is well known in the art. In particular, suitable constructions and arrangements for the containment flaps 37 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may include a front waist elastic member 131, a rear waist elastic member 132, and leg elastic members 133, as are known to those skilled in the art. The flap elastic members 36, the waist elastic members 131 and 132, and the leg elastic members 133 can be formed of any suitable elastic material that is well known to those skilled in the art.

The outer cover 21 may suitably include a material that is substantially liquid impermeable. The outer cover 21 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 21 is a 0.025 millimeter (1.0 mil) polyethylene film commercially available from Edison Plastics Company of South Plainfield, N.J. Alternatively, the outer cover 21 may include a woven or non-woven fibrous web layer that has been totally or partially constructed or treated to impart the desired levels of liquid impermeability to selected regions that are adjacent or proximate the absorbent structure. The outer cover 21 may also be stretchable, and in some aspects it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 23 is suitably compliant, soft-feeling, and non-irritating to the wearer's skin. The bodyside liner 23 is also sufficiently liquid permeable to permit liquid body exudates to readily penetrate through its thickness to the absorbent structure. A suitable liquid permeable bodyside liner 23 is a nonwoven polyethylene/polypropylene bicomponent web having a basis weight of about 27 gsm; the web may be spunbonded or a bonded carded web. Alternatively, the bodyside liner 23 may also be stretchable, and in some aspects it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding bodyside liner material.

An absorbent structure may be disposed between the outer cover 21 and the bodyside liner 23, which can be joined together by any suitable means such as adhesives, ultrasonic bonds, thermal bonds, or the like. While the illustrated absorbent structure is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure can be suitably compressible, conformable, non-irritating to a wearer's skin, and capable of absorbing and retaining liquids and certain body wastes. For example, the absorbent structure may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

Superabsorbent material may be suitably present in the absorbent structure in an amount of from about 0 to about 90 weight percent based on total weight of the absorbent structure. The absorbent structure may suitably have a density within the range of about 0.10 to about 0.35 grams per cubic centimeter. Superabsorbent materials are well known in the art and can be selected from natural, synthetic, and modified natural polymers and materials.

In one aspect, the absorbent structure 44 may be stretchable so as not to inhibit the stretchability of other components to which the absorbent structure may be adhered, such as the outer cover 21 and bodyside liner 23. For example, the absorbent structure may include materials disclosed in U.S. Pat. Nos. 5,964,743, 5,645,542, 6,231,557, 6,362,389, and international patent application WO 03/051254, the disclosure of each of which is incorporated by reference herein.

In some aspects, a surge management layer (not shown) may be located adjacent the absorbent structure (e.g., between the absorbent structure and the liner 23) and attached to various components of the article 20 such as the absorbent structure and/or the bodyside liner 23 by methods known in the art, such as by adhesive, ultrasonic or thermal bonding. A surge management layer helps to decelerate and diffuse surges or gushes of liquid that may be rapidly introduced into the absorbent structure of the article 20. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are incorporated by reference herein.

FIG. 3 shows an absorbent article in the form of a diaper 20. Diaper 20 includes many, but not all, of the features of the pants 20 in FIG. 2, and where the similarly numbered features can be made of the materials and methods described above for the training pants. Briefly, there is seen the outer cover 21 attached to the body side liner with an absorbent assembly 32 therebetween. At front waist edge 38 there is located a front waist elastic member 131. A crotch region is located between the front waist edge and back waist edge 39, with leg openings formed by leg elastic members 133 adjacent the crotch region when the diaper is fastened back to front and on a child. At back waist edge 39 there is located a back waist elastic member 132. Fastening tapes help maintain the diaper fastened back to front when on a wearer or child. The fastening tapes 11 can include any fastenable or refastenable fasteners suitable for absorbent articles, such as adhesive fasteners, cohesive fasteners, mechanical fasteners, or the like.

FIG. 4 shows another absorbent article similar to the diaper 20 seen in FIG. 3 in all respects except that this diaper also includes and on-article urine insult event device 40. Device 40 will be described in greater detail hereafter. In FIG. 4, the diaper 20 is fastened front to back by fastening tapes 11, and secured about the waist area of a child or wearer 8.

Figure 1:
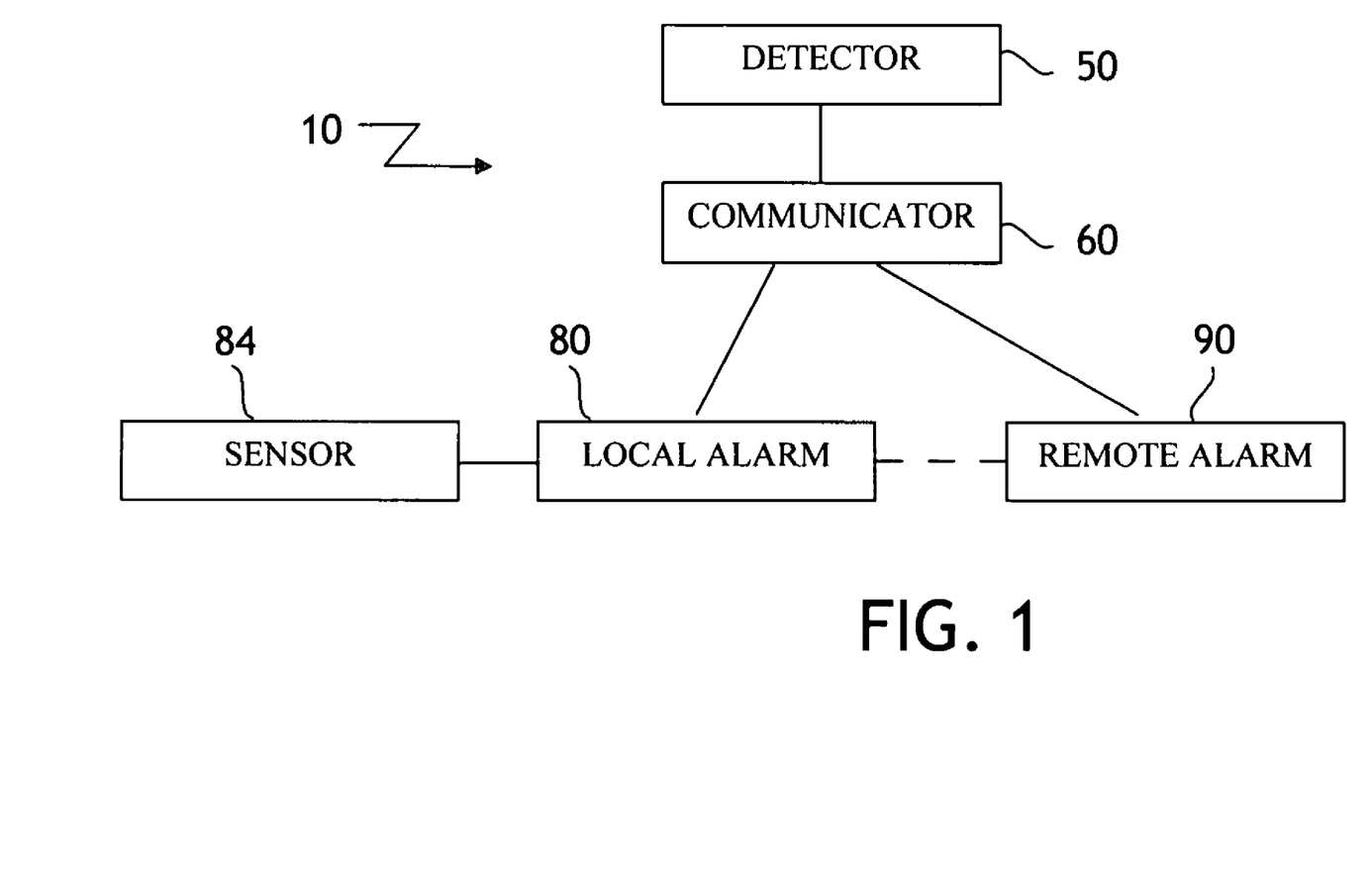
FIG. 1 representatively shows a schematic diagram of components of the present invention.

Referring to FIG. 1, there is representatively seen a system 10 for interactively training a child and a caregiver to assist the child to overcome bedwetting. The system includes an absorbent article (e.g., FIGS. 2-4) proximate the child, with the absorbent article having a urine insult detector 50 which detects a urine insult event. The urine insult detector 50 is operatively coupled with a urine insult event communicator 60 which communicates an occurrence of the urine insult event to a urine insult event alarm 80, 90. The urine insult event alarm includes a local alarm 80 proximate the child and a remote alarm 90 proximate the caregiver wherein the urine insult event alarm can inform both the child and the caregiver upon occurrence of the urine insult event and thereby provide a first interactive training opportunity to assist the child to overcome bedwetting. The local alarm 80 includes a sensor 84 which senses a condition of the child's environment in conjunction with the occurrence of the urine insult event. The remote alarm can be selectively activated and deactivated based on the condition and thereby provide a second interactive training opportunity to assist the child to overcome bedwetting.

Without being limited to a theory of understanding, it is believed that no two children train alike and thus an enuresis training system needs to be flexible to accommodate different children's different training needs. For example, early in the overnight training process, a child has little, if any, self ability to recognize that he/she needs to urinate and thus that she/he should wake up to do so. Additionally, children who experience nighttime wetting are often deep sleepers, and have little self ability to awaken to the informing of an alarm, e.g., by sound or other sensory action. At this early stage, a training system needs to be able to simultaneously inform the child and caregiver to the urine insult event so the caregiver can go the child and wake him/her each time there is a urine insult event. The simultaneous action could occur automatically as part of the system 10, such that local alarm 80 and remote alarm 90 both inform (e.g., by some sensory means such as audible, tactile or visual) the respective child and caregiver to cause him/her to wake, or at least awaken the caregiver in his/her sleeping location remote from the child so he/she can then come to the child to help wake him/her. Alternatively, the simultaneous action could occur through use of a sensor 84 that is in communication with the communicator 60, the local alarm 80 and/or the remote alarm 90. The sensor would sense a condition of the child's environment (e.g., the child in a prone body position or the absence of effective presence of light energy, each of these indicating the child is still asleep) and then cause the local alarm 80 and remote alarm 90 to both inform (e.g., by some sensory means such as audible, tactile or visual) the respective child and caregiver to cause them to wake, or at least awaken the caregiver in his/her sleeping location remote from the child so he/she can then come to the child to help wake him/her.

As the child advances in training development, a training system needs to be able to selectively inform the child and caregiver to the urine insult event so the caregiver can go to the child only when needed to wake him/her if there is a urine insult event that the child does not wake up for. The selective action could occur as part of the system 10, such that local alarm 80 first informs (e.g., by some sensory means such as audible, tactile or visual) the child and the remote alarm is delayed (e.g., for anywhere from a few seconds to many seconds to 30 seconds, to a minute or more) in informing the caregiver so the child can first on his/her own have the opportunity to cause him/her self to wake and then only after the delay period the adult is informed to awaken the caregiver in his/her sleeping location remote from the child so he/she can then come to the child to help wake him/her. Alternatively, the selective action could occur through use of sensor 84 that is in communication with the communicator 60, the local alarm 80 and/or the remote alarm 90. For example, after the delay (e.g., for anywhere from a few seconds to many seconds to 30 seconds, to a minute or more) in informing the caregiver so the child can first on his/her own have the opportunity to cause him/her self to wake, the sensor would sense a condition of the child's environment (e.g., the child in a prone body position or the absence of effective presence of light energy, each of these indicating the child is still asleep) and then cause the remote alarm 90 to inform (e.g., by some sensory means such as audible, tactile or visual) the caregiver to cause him/her to wake so he/she can then come to the child to help wake him/her. As another example, the sensor would sense a condition of the child's environment (e.g., the child in an upright body position, the effective presence of light energy (e.g., the child turning on a light), or local alarm deactivation by the child (e.g., the child turning off the alarm after the local alarm wakes the child up), and this would cause the remote alarm to not be activated, or if activated but not yet informing the caregiver, then deactivating the remote alarm before it would inform the caregiver.

In the situations where there is selective activation or deactivation of the remote alarm before informing the caregiver, there is the opportunity to reinforce the child's confidence in his/her ability to toilet train on their own, even at night, even if the caregiver is delayed for only a few seconds before checking on the child. Also, when the local alarm does inform the child but the remote alarm is not activated or is deactivated, there is the opportunity to not disturb the caregiver unnecessarily at all during the night when the child has made significant progress toward waking him/her self and caregiver intervention is no longer needed or not needed as regularly. In these ways when the caregiver is not even informed of the urine insult event (and thus can pleasantly sleep through the night) he/she is still passively informed that the child is making progress toward overcoming bedwetting without active caregiver interaction, and will realize such the next morning. At the time of the urine insult event when he/she wakes and the child's environment is such that the remote alarm was not activated or was deactivated, the child is provided a second interactive training opportunity to assist the child to overcome bedwetting by self awareness (i.e., if the child is conscious enough at this time) or by caregiver interaction the next morning when the caregiver realizes he/she did not need to wake for the child.

Figure 5A:
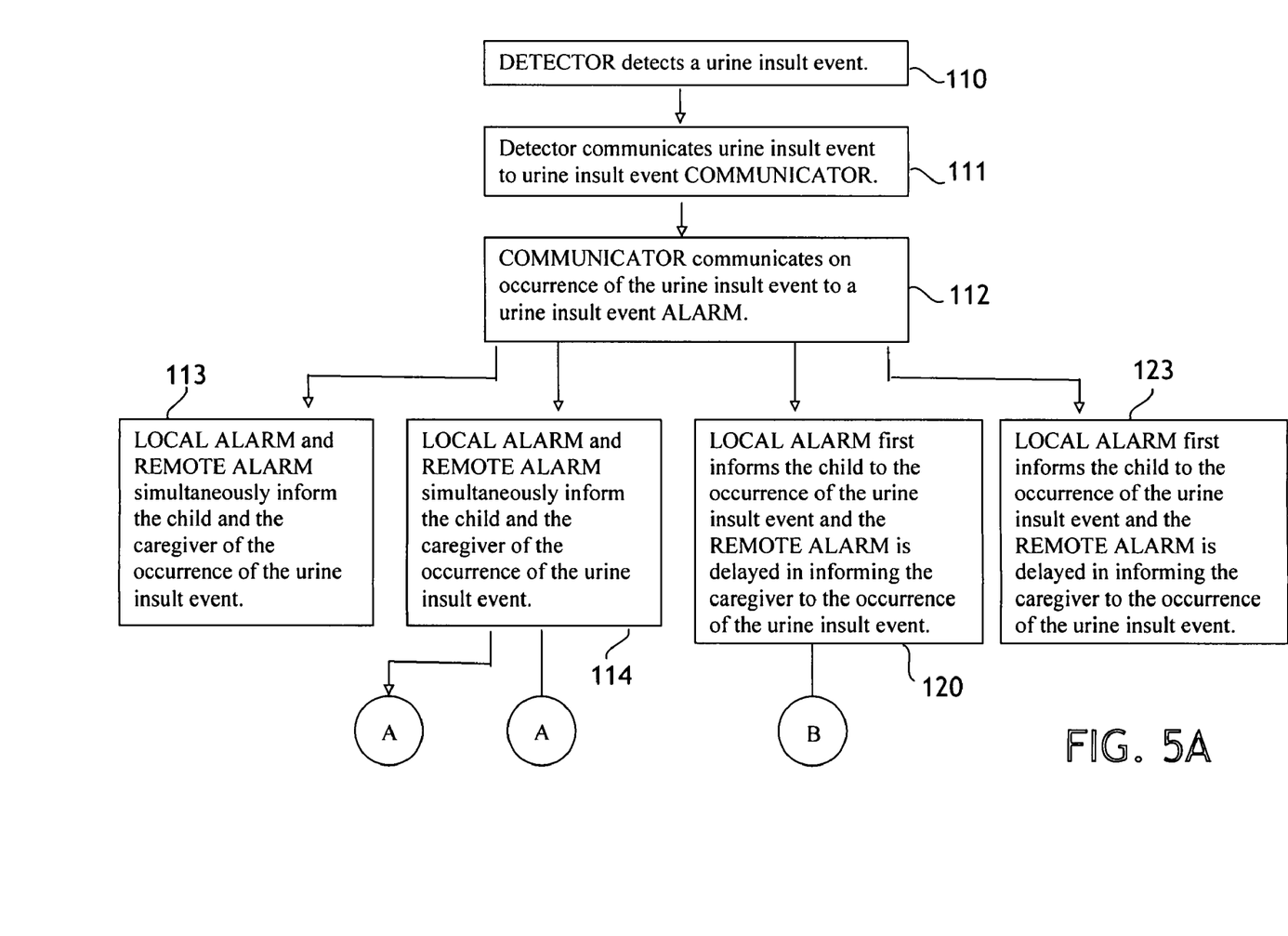
Figure 5B:
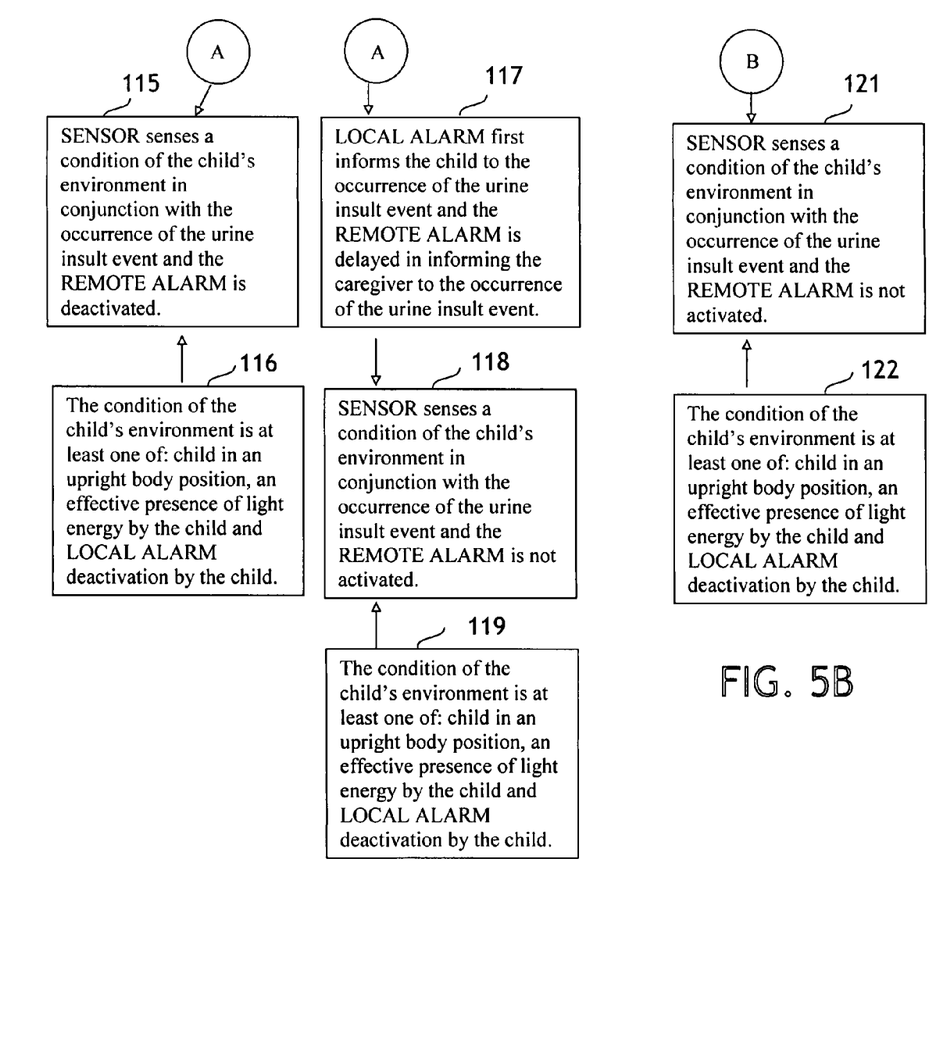

With reference to FIGS. 5A and 5B, other configurations of the present invention are depicted, all which help accommodate different children's different training needs. System 10 (FIG. 1) can be configured, after following common path 110, 111 and 112, to follow any of the paths (i) 113, (ii) 114, 115, 116, (iii) 114, 117, 118, 119, (iv) 120, 121, 122, (v) 123. For example, the system 10 of path 113 means that the local alarm and remote alarm simultaneously inform the child and the caregiver every time upon a urine insult event and thereby provide an interactive training opportunity to assist the child to overcome bedwetting.

As another example, the system 10 of path 114, 115, 116, means in a first mode the urine insult event alarm informs the child and the caregiver simultaneously of the occurrence of the urine insult event and thereby provide an interactive training opportunity to assist the child to overcome bedwetting. Further, the local alarm includes a sensor which senses a condition of the child's environment in conjunction with the occurrence of the urine insult event and the remote alarm is in a first mode deactivated based on the condition and thereby provides another interactive training opportunity to assist the child to overcome bedwetting. The condition of the child's environment can be the child's upright body position, effective presence of light energy or local alarm deactivation by the child.

As yet another example, the system 10 of path 114, 117, 118, 119, means in a first mode the urine insult event alarm informs the child and the caregiver simultaneously of the occurrence of the urine insult event and thereby provides an interactive training opportunity to assist the child to overcome bedwetting. Further, in a second mode the local alarm informs the child first to the occurrence of the urine insult event and the remote alarm is delayed in informing the caregiver to the occurrence of the urine insult event and thereby provides another interactive training opportunity to assist the child to overcome bedwetting. Still further, the local alarm includes a sensor which senses a condition of the child's environment in conjunction with the occurrence of the urine insult event and the remote alarm is in a second mode not activated based on the condition and thereby provides another interactive training opportunity to assist the child to overcome bedwetting. The condition of the child's environment can be the child's upright body position, effective presence of light energy or local alarm deactivation by the child.

As still another example, the system 10 of path 120, 121, 122, means in a second mode the local alarm informs the child first to the occurrence of the urine insult event and the remote alarm is delayed in informing the caregiver to the occurrence of the urine insult event and thereby provides another interactive training opportunity to assist the child to overcome bedwetting. Further, the local alarm includes a sensor which senses a condition of the child's environment in conjunction with the occurrence of the urine insult event and the remote alarm is in a second mode not activated based on the condition and thereby provides another interactive training opportunity to assist the child to overcome bedwetting. The condition of the child's environment can be the child's upright body position, effective presence of light energy or local alarm deactivation by the child.

As yet still another example, path 123 means that the local alarm informs the child first to the occurrence of the urine insult event and the remote alarm is delayed in informing the caregiver to the occurrence of the urine insult event and thereby provides an interactive training opportunity to assist the child to overcome bedwetting. In this example, after a set period of time the caregiver is informed by the remote alarm regardless of the condition of the child's environment and thereby provides another interactive training opportunity to assist the child to overcome bedwetting.

And additionally, the training path can depart from the above examples and/or use parts of one path with parts of another path, to be modified to meet individual needs of the child. Also, regression in training progress is fairly common, and a child may need to repeat any or all of the training steps, or may end up having a slightly different training experience the second, third, etc. time around. It should be understood that while the examples in FIGS. 5A and 5B make training appear to be a straight through linear process, it can be more of a one step forward progress, two steps backward loss of progress, activity. Thus, the scope of the present invention encompasses these variations as long as such variations are also consistent with the necessary teachings of the invention.

Referring to FIGS. 2-4, some hardware for use with the invention is seen. FIGS. 2 and 3 depict an example of a urine insult detector 50, which detector 50 may have one or more leads 51 therewith going to a urine insult event area 52. Detector 50 can be located in the absorbent article 20, or it may be located away from the absorbent article to do absorbent article sampling (e.g., infrared technology or other off child remote sampling technologies). The detector 50 may be operatively coupled with the urine insult event communicator (FIG. 1) by hard wiring, wireless communication or other conventional communication technology. Each of the communicator 60, local alarm 80, sensor 84 and remote alarm 90, each may be hard wired to each other or, more preferably, can use wireless communication or other conventional communication technology to interact with one another as taught in the present invention.

As seen in FIG. 4, there may be a urine insult event device 40 directly attached to the absorbent article. Device 40 may include one or more of the detector 50, communicator 60, local alarm 80 and sensor 84. Alternatively, one or more of the detector 50, communicator 60, local alarm 80 and sensor 84 may be located in a structure removed from the child and/or the absorbent article, yet still proximate the child (e.g., beside a bed, or on a night stand, on a table in the room with the child, and the like). Sensor 90 is preferably located proximate the caregiver (e.g., beside a bed, or on a night stand, on a table in the room with the caregiver, and the like).

A variety of conventional technologies can be used to practice the present invention, and one of ordinary skill in the art would know how to do so in combination with the teachings of the present invention. It is not the technology that is important, but rather what matters is that the technology is configured according to one or more of the teachings of the present invention. For example, sample technologies are any of those taught in this patent application assignee's granted Jun. 24, 2003 U.S. Pat. No. 6,583,722 of Juetter et al. titled "Wetness Signaling Device".

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A system for interactively training a child and a caregiver to assist the child to overcome bedwetting, comprising:
    an absorbent article proximate the child, the absorbent article includes a urine insult detector which detects a urine insult event;
    the urine insult detector is operatively coupled with a urine insult event communicator which communicates an occurrence of the urine insult event to a urine insult event alarm;
    the urine insult event alarm includes a local alarm proximate the child and a remote alarm proximate the caregiver wherein the urine insult event alarm can inform both the child and the caregiver upon occurrence of the urine insult event and thereby provide a first interactive training opportunity to assist the child to overcome bedwetting; and,
    the local alarm includes a sensor which senses a condition of the child's environment in conjunction with the occurrence of the urine insult event and wherein the remote alarm can be selectively activated and deactivated based on the condition and thereby provide a second interactive training opportunity to assist the child to overcome bedwetting.

2. The system of claim 1 wherein the absorbent article comprises an absorbent article garment of a training pant or a diaper.

3. The system of claim 2 wherein the local alarm is located in or on the absorbent article garment.

4. The system of claim 1 wherein the local alarm is located in a structure removed from contact with the child yet proximate the child.

5. The system of claim 1 wherein the urine insult event alarm informs the child and the caregiver simultaneously of the occurrence of the urine insult event and thereby provides the first interactive training opportunity to assist the child to overcome bedwetting.

6. The system of claim 1 wherein the local alarm informs the child first to the occurrence of the urine insult event and the remote alarm is delayed in informing the caregiver to the occurrence of the urine insult event and thereby provides the first interactive training opportunity to assist the child to overcome bedwetting.

7. The system of claim 1 wherein the remote alarm is not activated or is deactivated based on the condition and thereby provides the second interactive training opportunity to assist the child to overcome bedwetting.

8. The system of claim 7 wherein the condition of the child's environment comprises a member from the group consisting of: child upright body position, effective presence of light energy and local alarm deactivation by the child, each of these which thereby passively inform the caregiver that the child is making progress toward overcoming bedwetting without active caregiver interaction.

9. A system for interactively training a child and a caregiver to assist the child to overcome bedwetting, comprising:

an absorbent article proximate the child, the absorbent article includes a urine insult detector which detects a urine insult event;

the urine insult detector is operatively coupled with a urine insult event communicator which communicates an occurrence of the urine insult event to a urine insult event alarm;

the urine insult event alarm includes a local alarm proximate the child and a remote alarm proximate the caregiver wherein the local alarm informs the child first to the occurrence of the urine insult event and the remote alarm is delayed in informing the caregiver to the occurrence of the urine insult event and thereby provides a first interactive training opportunity to assist the child to overcome bedwetting; and, the local alarm includes a sensor which senses a condition of the child's environment in conjunction with the occurrence of the urine insult event and wherein the remote alarm is not activated based on the condition and thereby provides a second interactive training opportunity to assist the child to overcome bedwetting.

10. The system of claim 9 wherein the absorbent article comprises an absorbent article garment of a training pant or a diaper.

11. The system of claim 10 wherein the local alarm is located in or on the absorbent article garment.

12. The system of claim 9 wherein the local alarm is located in a structure removed from contact with the child yet proximate the child.

13. The system of claim 9 wherein the condition of the child's environment comprises a member from the group consisting of: child upright body position, effective presence of light energy and local alarm deactivation by the child, each of these which thereby passively inform the caregiver that the child is making progress toward overcoming bedwetting without active caregiver interaction.

14. A system for interactively training a child and a caregiver to assist the child to overcome bedwetting, comprising:

an absorbent article proximate the child, the absorbent article includes a urine insult detector which detects a urine insult event;

the urine insult detector is operatively coupled with a urine insult event communicator which communicates an occurrence of the urine insult event to a urine insult event alarm;

the urine insult event alarm includes a local alarm proximate the child and a remote alarm proximate the caregiver wherein (i) in a first mode the urine insult event alarm informs the child and the caregiver simultaneously of the occurrence of the urine insult event and thereby provides a first interactive training opportunity to assist the child to overcome bedwetting and (ii) in a second mode the local alarm informs the child first to the occurrence of the urine insult event and the remote alarm is delayed in informing the caregiver to the occurrence of the urine insult event and thereby provides a second interactive training opportunity to assist the child to overcome bedwetting; and, the local alarm includes a sensor which senses a condition of the child's environment in conjunction with the occurrence of the urine insult event and wherein the remote alarm is (i) in the first mode deactivated based on the condition and thereby provides a third interactive training opportunity to assist the child to overcome bedwetting and (ii) in the second mode is not activated based on the condition and thereby provides a fourth interactive training opportunity to assist the child to overcome bedwetting.

15. The system of claim 14 wherein the absorbent article comprises an absorbent article garment of a training pant or a diaper.

16. The system of claim 15 wherein the local alarm is located in or on the absorbent article garment.

17. The system of claim 14 wherein the local alarm is located in a structure removed from contact with the child yet proximate the child.

18. The system of claim 17 wherein the condition of the child's environment comprises a member from the group consisting of: child upright body position, effective presence of light energy and local alarm deactivation by the child, each of these which thereby passively inform the caregiver that the child is making progress toward overcoming bedwetting without active caregiver interaction.

* * * * *